United States Patent [19]

Bolton et al.

[11] 4,003,889
[45] Jan. 18, 1977

[54] 1,3-DIARYL-2-PYRAZOLINE DERIVATIVES

[75] Inventors: Ivan Joseph Bolton, Bingley; Alec Victor Mercer, Leeds, both of England; Fritz Fleck, Bottmingen, Switzerland

[73] Assignee: Sandoz Ltd., Basel, Switzerland

[22] Filed: June 17, 1974

[21] Appl. No.: 480,128

[30] Foreign Application Priority Data

June 21, 1973 United Kingdom ............ 29478/73
Nov. 16, 1973 United Kingdom ............ 53255/73
Feb. 15, 1974 United Kingdom ............. 6952/74

[52] U.S. Cl. .................. 260/239.9; 260/310 D
[51] Int. Cl.² ............ C07D 231/42; C07D 233/00; C07D 235/00; C07D 261/16
[58] Field of Search .................. 260/239.9, 310 D

[56] References Cited

UNITED STATES PATENTS

| 3,378,389 | 4/1968 | Schellhammer et al. | 117/33.5 |
|---|---|---|---|
| 3,522,242 | 7/1970 | Schinzel et al. | 260/239.9 |
| 3,560,485 | 2/1971 | Schinzel et al. | 260/239.8 |
| 3,629,241 | 12/1971 | Krause et al. | 260/239.9 |
| 3,690,947 | 9/1972 | Roach et al. | 117/33.5 |
| 3,849,406 | 11/1974 | Aebli et al. | 260/239.9 |

FOREIGN PATENTS OR APPLICATIONS

| 1,445,705 | 1/1969 | Germany |
|---|---|---|
| 1,204,953 | 9/1970 | United Kingdom |

Primary Examiner—Albert T. Meyers
Assistant Examiner—D. W. Robinson
Attorney, Agent, or Firm—Gerald D. Sharkin; Richard E. Vila; Joseph J. Borovian

[57] ABSTRACT

Disclosed are compounds of formula I,

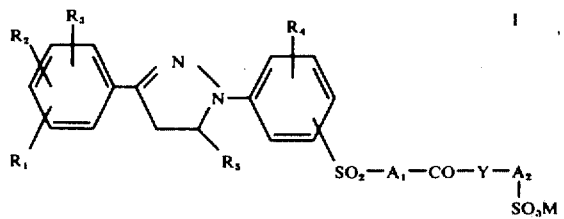

in which either
$R_1$, $R_2$ and $R_3$, which may be the same or different, each signifies a hydrogen atom, a chlorine or fluorine atom, an alkyl radical of 1 to 4 carbon atoms, an alkoxy radical of 1 to 4 carbon atoms, a cyano group, a group —$SO_3M$, an unsubstituted phenyl radical or a phenyl radical substituted by up to 2 substituents selected from chlorine, fluorine, alkyl of 1 to 4 carbon atoms, alkoxy of 1 to 4 carbon atoms and the group —$SO_3M$, with the proviso that only one of $R_1$, $R_2$ and $R_3$ signifies an unsubstituted or substituted phenyl radical, or two of $R_1$, $R_2$ and $R_3$ together form a methylenedioxy group, the other of $R_1$, $R_2$ and $R_3$ having one of the above significances, $R_4$ signifies a hydrogen atom, a chlorine or fluorine atom, an alkyl radical of 1 to 4 carbon atoms or an alkoxy radical of 1 to 4 carbon atoms, $R_5$ signifies a hydrogen atom, an alkyl radical of 1 to 4 carbon atoms, an unsubstituted phenyl radical or a phenyl radical substituted by 1 or 2 substituents selected from chlorine, fluorine, alkyl of 1 to 4 carbon atoms, alkoxy of 1 to 4 carbon atoms and the group —$SO_3M$, $A_1$ signifies a $C_1$ to $C_3$ alkylene chain, unsubstituted or substituted by up to two alkyl groups of 1 to 4 carbon atoms, $A_2$ signifies a $C_1$ to $C_3$ alkylene chain, unsubstituted or substituted by up to two alkyl groups of 1 to 4 carbon atoms; or a phenylene group, unsubstituted or substituted by up to 2 substituents selected from chlorine, fluorine, alkyl of 1 to 4 carbon atoms, alkoxy of 1 to 4 carbon atoms and the group —$SO_3M$, Y signifies —O— or —$NR_6$—, in which $R_6$ signifies a hydrogen atom or an alkyl radical of 1 to 4 carbon atoms, and the Ms, which may be the same or different, each signifies a hydrogen atom, or a non-chromophoric cation: their production and use as optical brightening agents particularly for textile substrates comprising polyamide fibers.

30 Claims, No Drawings

1,3-DIARYL-2-PYRAZOLINE DERIVATIVES

The invention relates to pyrazoline compounds. The invention provides compounds of formula I,

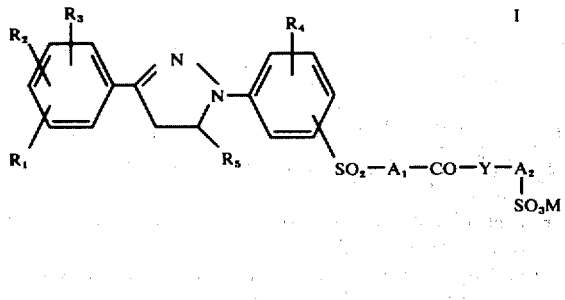

in which either
R$_1$, R$_2$ and R$_3$, which may be the same or different, each signifies a hydrogen atom, a chlorine or fluorine atom, an alkyl radical of 1 to 4 carbon atoms, an alkoxy radical of 1 to 4 carbon atoms, a cyano group, a group —SO$_3$M, an unsubstituted phenyl radical or a phenyl radical substituted by up to 2 substituents selected from chlorine, fluorine, alkyl of 1 to 4 carbon atoms, alkoxy of 1 to 4 carbon atoms and the group —SO$_3$M, with the proviso that only one of R$_1$, R$_2$ and R$_3$ signifies an unsubstituted or substituted phenyl radical, or two of
R$_1$, R$_2$ and R$_3$ together form a methylenedioxy group, the other of R$_1$, R$_2$ and R$_3$ having one of the above significances, R$_4$ signifies a hydrogen atom, a chlorine or fluorine atom, an alkyl radical of 1 to 4 carbon atoms or an alkoxy radical of 1 to 4 carbon atoms, R$_5$ signifies a hydrogen atom, an alkyl radical of 1 to 4 carbon atoms, an unsubstituted phenyl radical or a phenyl radical substituted by 1 or 2 substituents selected from chlorine, fluorine, alkyl of 1 to 4 carbon atoms, alkoxy of 1 to 4 carbon atoms and the group —SO$_3$M, A$_1$ signifies a C$_1$ to C$_3$ alkylene chain unsubstituted or substituted by up to two alkyl groups of 1 to 4 carbon atoms, A$_2$ signifies a C$_1$ to C$_3$ alkylene chain, unsubstituted or substituted by up to two alkyl groups of 1 to 4 carbon atoms; or a phenylene group, unsubstituted or substituted by up to 2 substituents selected from chlorine, fluorine, alkyl of 1 to 4 carbon atoms, alkoxy of 1 to 4 carbon atoms and the group —SO$_3$M, Y signifies —O— or —NR$_6$—, in which R$_6$ signifies a hydrogen atom or an alkyl radical of 1 to 4 carbon atoms, and the Ms, which may be the same or different, each signifies a hydrogen atom, or a non-chromophoric cation.

The invention also provides a process for the production of compounds of formula I, characterised by a. reacting a compound of formula II,

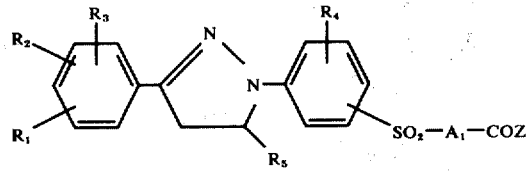

in which
R$_1$, R$_2$, R$_3$, R$_4$, R$_5$ and A$_1$ are as defined above, and Z signifies a halogen atom, a hydroxy group or an alkoxy radical of 1 to 2 carbon atoms, with a compound of formula III,

in which Y, A$_2$ and M are as defined above, b. reacting a compound of for formula IV,

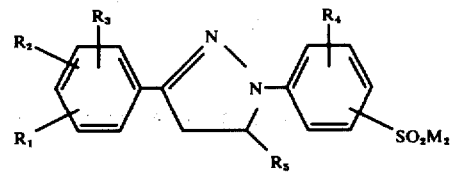

in which
R$_1$, R$_2$, R$_3$, R$_4$ and R$_5$ are as defined above, and M$_2$ signifies a hydrogen atom or an alkali metal cation, with a compound of formula V,

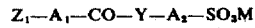

in which A$_1$, A$_2$, Y and M are as defined above, and Z$_1$ signifies a halogen atom, c. reacting a compound of formula VI,

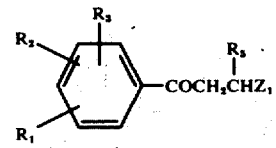

in which R$_1$, R$_2$, R$_3$, R$_5$ and Z$_1$ are as defined above, with a compound of formula VII,

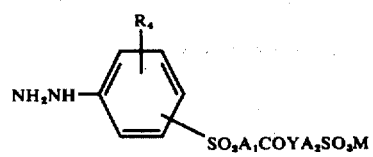

in which $R_4$, $A_1$, $A_2$, Y and M are defined above, d. reacting a compound of formula VIII,

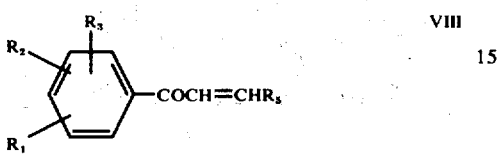

VIII in which
$R_1$, $R_2$, $R_3$ and $R_5$ are as defined above, with a compound of formula VII, stated above, e. obtaining a compound of formula Ia,

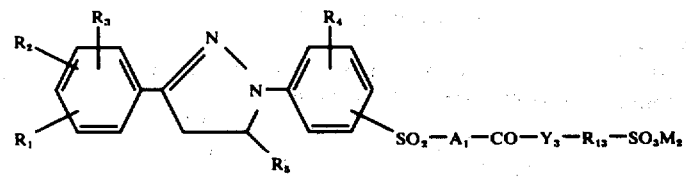

Ia in which,
$R_1$, $R_2$, $R_3$, $R_4$, $R_5$, $A_1$ and $M_2$ are as defined above, $Y_3$ signifies —O— or $NR_6$ —, in which $R_6$ is as defined above, and $R_{13}$ signifies a $C_2$ or $C_3$ alkylene chain, unsubstituted or substituted by up to two alkyl radicals of 1 to 4 carbon atoms,
by reacting a compound of formula IX,

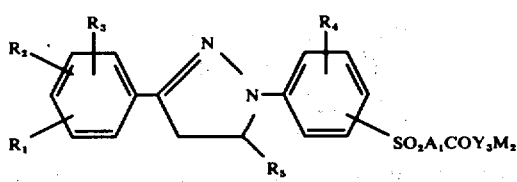

IX in which $R_1$, $R_2$, $R_3$, $R_4$, $R_5$, $A_1$, $Y_3$ and $M_2$ are as defined above,
with a compound of formula X, $$\underset{SO_2 \quad\quad O}{\overset{R_{13}}{\triangle}}$$

X in which $R_{13}$ is as defined above, f. obtaining a compound of formula Ib,

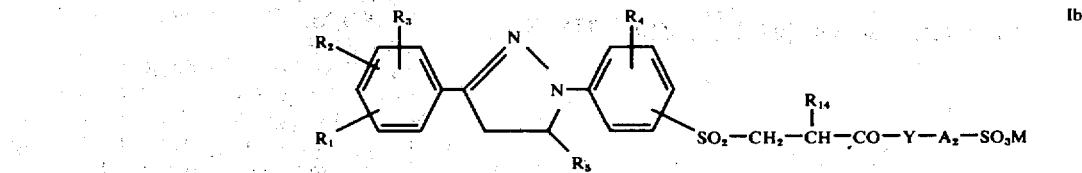

Ib in which
$R_1$, $R_2$, $R_3$, $R_4$, $R_5$, Y, $A_2$ and M are as defined above, and
$R_{14}$ signifies a hydrogen atom or an alkyl radical of 1 to 4 carbon atoms,
by reacting a compound of formula IV, stated above, with a compound of formula XI,

XI in which $R_{14}$, Y, $A_2$ and M are as defined above, or g. obtaining a compound of formula Ic,

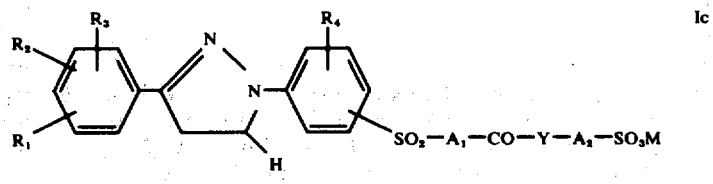

Ic in which
$R_1$, $R_2$, $R_3$, $R_4$, $A_1$, Y and M are as defined above, by reacting a compound of formula XII,

XII

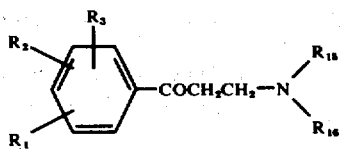

in which
$R_1$, $R_2$ and $R_3$ are as defined above,
and either

R₁₅ and R₁₆, which may be the same or different, each signifies a hydrogen atom or an alkyl radical of 1 to 4 carbon atoms, or R₁₅ and R₁₆, together with the nitrogen atom to which they are attached, signify a heterocyclic ring which optionally contains a further hetero atom to the nitrogen atom, with a compound of formula VII, stated above.

The above processes may be carried out in manner conventional for the types of reaction involved.

Process a) is suitably carried out in water, a polar organic solvent or in an aqueous organic solvent, such as in aqueous acetone, aqueous dimethylformamide or aqueous dioxan. A suitable reaction temperature is from 0° to 150° C, preferably from 0° to 50° C. Where, in the compound of formula II, Z signifies a halogen atom, the reaction is suitably carried out in the presence of a base acceptor, such as sodium carbonate or sodium hydroxide and, where Z signifies a hydroxy or alkoxy radical, in the presence of an acid catalyst such as sulphuric acid, hydrogen chloride or p-toluenesulphonic acid.

Process b) may suitably be carried out in water, a polar organic solvent or in an aqueous organic solvent medium, such as in aqueous ethanol or isopropanol, aqueous acetone, aqueous dioxan or aqueous dimethylformamide. A suitable reaction temperature is from 20° to 150 C, preferably from 80° to 150° C. The reaction is suitably carried out at a pH of from 3 to 10, preferably from 4 to 8.

Process c) may be carried out in water, a polar organic solvent or in an aqueous organic solvent medium, such as aqueous ethanol, isopropanol, acetic acid or dimethylformamide. A suitable reaction temperature is from 20° to 200° C, preferably from 50° to 150° C. The reaction is suitably carried out at a pH of from 1 to 10, preferably from 2 to 6.

Process d) is conveniently carried out in water or a polar organic solvent such as ethanol, isopropanol, dioxan or dimethylformamide, in the presence or absence of water. A suitable reaction temperature is from 20° to 150° C, preferably from 50° to 120° C. The reaction is suitably carried out under acidic conditions, e.g. at a pH of from 1to 6, preferably from 2 to 4.

Process e) is conveniently carried out in an inert organic solvent such as in acetone, dimethylformamide or dioxan. A suitable reaction temperature is from 20° to 200° C, preferably from 50° to 150° C.

Process f) is conveniently carried out in water, a polar organic solvent or in an aqueous organic solvent, such as in aqueous ethanol, isopropanol, cellosolve, acetone, dioxan or dimethylformamide. A suitable reaction temperature is from 20° to 150° C, preferably from 50° to 150° C. The reaction may conveniently be carried out under from mildly acidic to mildly basic conditions, e.g. from pH 3 to 9, preferably from 4 to 8.

Process g) may be carried out in water or in an organic solvent, such as in ethanol, isopropanol, dioxan or cellosolve, in the presence or absence of water. A suitable reaction temperature is from 20° to 200° C, preferably from 50° to 150° C. The reaction is conveniently carried out under acid or basic conditions, e.g. from pH 2 to 10, preferably under neutral to mildly basic conditions, e.g. from pH 6 to 9.

In the compound of formula XII, it will be appreciated that the group —NR₁₅R₁₆ is a leaving group and hence the exact significance of R₁₅ and R₁₆, when such form a heterocyclic ring with the nitrogen atom, is of little importance provided that the leaving properties are not detrimentally affected. As examples of the significance of —NR₁₅R₁₆ may be given the morpholino, piperidino and pyrrolidino radicals.

The compounds of formulae II, III, IV, V, VI, VII, VIII, IX, X, XI and XII are either known or may be obtained in conventional manner from available starting materials.

Of particular interest as intermediate compounds in the production of compounds of formula I are the compounds of formulae IIa and IVa

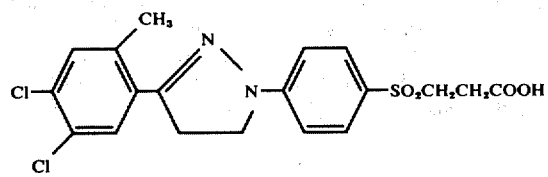

and salts thereof

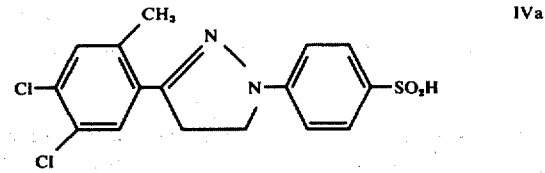

and salts thereof.

The salt forms of compound IIa may be converted into free acid form and used in process a), described above. Similarly, the compounds of formula IVa in salt form other than alkali-metal salt form, can be converted into free acid or alkali-metal salt form and used in process b), described above. The preparation of the compound of formula IIa, in free acid form is described in Example 4, hereinafter. Such free acid form may be converted into salt form, e.g. with a cation M, in conventional manner. The preparation of the compound of formula IVa in sodium salt form is described in Example 6, hereinafter. Such salt form may be converted into free acid form or other salt form, e.g. with a cation M, in conventional manner.

The resulting compounds of formula I may be isolated and purified in conventional manner. As will be appreciated, conversion of compounds of formula I in free acid form, to salt forms and vice versa may be carried out, as desired, in conventional manner, as can interconversion of salt forms. As indicated above, where the compounds of formula I contain a plurality of —SO₃M groups, the M's may be the same or different. Thus, partial and mixed salt forms of the compounds are embraced by the invention.

The exact nature of M, when such is a cation, is not critical provided such cation is non-chromophoric. As examples of preferred cations may be given the alkali-metal cations, such as sodium and potassium cations and ammonium and alkylammonium cations, e.g. cations of formula $R_7R_8R_9R_{10}N^+$, in which $R_7$, $R_8$, $R_9$ and $R_{10}$, independently, each signify a hydrogen atom or an alkyl radical of 1 to 4 carbon atoms, unsubstituted or substituted by up to two substituents selected from alkyl of up to 2 carbon atoms and hydroxy. Preferably at least one of $R_7$, $R_8$, $R_9$ and $R_{10}$ signifies hydrogen. As examples of specific cations of such formula may be given the diethanolammonium and tri-isopropanolammonium cations.

ylene radical further substituted by a $-SO_3M$ or $C_{1-4}$alkyl, preferably methyl, group, and
Y' signifies

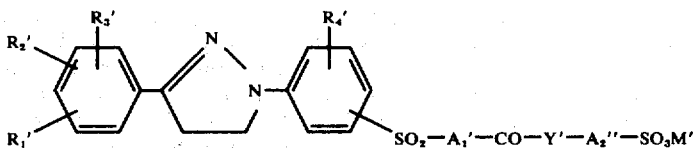

in which $R_6'$ sigifies a hydrogen atom or an alkyl radical of up to 2 carbon atoms.

Representative of the compounds of formula I' may be given the compounds of formula Ia'

Ia'

In the compounds of formula I, any phenyl radical as $R_1$, $R_2$ or $R_3$ is preferably unsubstituted. Preferably at most only one of $R_1$, $R_2$ and $R_3$ signifies a group selected from $-SO_3M$ and cyano. Where two of $R_1$, $R_2$ and $R_3$, together, signify methylenedioxy, the other preferably signifies other than phenyl. Indeed, where a methylenedioxy substituent is present, such is preferably the sole substituent. Any alkyl radical as a substituent on an alkylene chain as $A_1$ or $A_2$ is preferably of 1 or 2 carbon atoms, most preferably a methyl group.

Preferred compounds of formula I are the compounds of formula I'.

in which
$R_1'$, $R_2'$, $R_3'$, $R_4'$, M, $A_1'$ and Y' are as defined above, and
$A_2''$ signifies an unsubstituted $C_1$–$C_3$ alkylene chain, the compounds of formula Ib'

Ib' in which
$R_2'''$ signifies chlorine and
either
$R_1'''$ and $R_3'''$ both signify hydrogen,
or
$R_1'''$ signifies chlorine and
$R_3'''$ signifies methyl,

I' in which M is as defined above,
$R_1'$, $R_2'$ and $R_3'$, independently, each signifies a hydrogen atom, a chlorine or fluorine atom or an alkyl or alkoxy radical of 1 to 4 carbon atoms,
$R_4'$ signifies a hydrogen atom, a chlorine or fluorine atom or an alkyl or alkoxy radical of 1 to 4 carbon atoms, preferably a hydrogen atom,
$R_5'$ signifies hydrogen, $C_{1-4}$ alkyl, preferably methyl, or phenyl,
$A_1'$ signifies an unsubstituted $C_1$–$C_3$ alkylene chain,
$A_2'$ signifies an unsubstituted $C_1$–$C_3$ alkylene chain, a further unsubstituted phenylene radical or a phen- $A_1'''$ signifies an unsubstituted alkylene radical of up to 2 carbon atoms,
Y'''' signifies $-O-$, $-NH-$ or $$-\underset{|}{\underset{CH_3}{N}}-$$

$A_2'''$ signifies a further unsubstituted phenylene radical, preferably a further unsubstituted 1,3- or 1,4-phenylene radical, or an alkylene radical of two carbon atoms, and M is as defined above,
and the compounds of formula Ic'

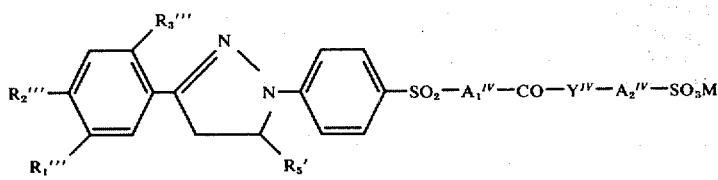

in
R$_1'''$, R$_2'''$, R$_3'''$, R$_5'$ and M are as defined above,
A$_1^{IV}$ signifies an unsubstituted alkylene radical of up to 2, preferably of 2, carbon atoms,
A$_2^{IV}$ signifies an ethylene group, a further unsubstituted phenylene radical or a phenylene radical substituted by a —SO$_3$M or C$_{1-4}$ alkyl, preferably methyl, group, and
Y$^{IV}$ signifies –O –, —NH — or

preferably -NH- or

The preferred compounds of formula Ia' are the compounds of formula Ia''

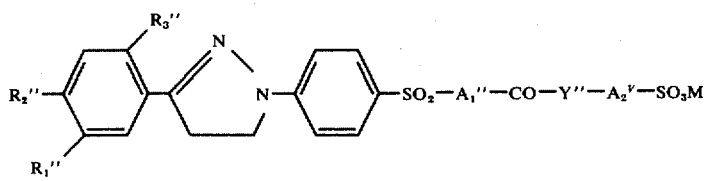

in which
R$_1''$, R$_2''$ and R$_3''$, which may be the same or different, each signifies a hydrogen atom, a chlorine atom or an alkyl radical of up to 2 carbon atoms,
Y'' signifies -O—, —NH- or

A$_1''$ signifies an unsubstituted alkylene radical of up to 2 carbon atoms,
A$_2''$ signifies an unsubstituted alkylene radical of 2 to 3 carbon atoms, and M is as defined above.

As examples of alkyl and alkoxy radicals in the compounds of formulae I, I', Ia' and Ic', may be given methyl, ethyl, n-propyl, iso-propyl and butyl, and methoxy, ethoxy, n-propyloxy, iso-propyloxy and butoxy.

In the compounds of formula I, I', Ia', Ib', Ic'' and Ia, M preferably signifies hydrogen, an alkali metal cation, preferably a sodium ion, or an ion of formula R$_7$R$_8$R$_9$NH,$^+$ in which R$_7$, R$_8$ and R$_9$ are as defined above, preferably the ammonium cation. The most preferred significances of M are hydrogen and sodium.

In the compounds of formula I' and Ia', R$_4'$ preferably signifies hydrogen. Indeed, in compounds of formula I, R$_4$ preferably signifies hydrogen. Further, in the compounds of formula I, and Ia' and —SO$_2$A'-COY'—A$_2'$-COY'—A$_2'$(A$_2''$) —SO$_3$M group is preferably in the para-position of the phenyl ring to which it is attached.

The compounds of formula I are useful as optical brightening agents, giving good results on natural or synthetic polyamide fibres, particularly on nylon 6 or nylon 6,6 fibres. Thus, the invention also provides a process for optically brightening a fibrous substrate, preferably of natural or synthetic polyamide fibres, particularly nylon 6 or nylon 6,6 fibres, comprising applying thereto, as brightening agent, a compound of formula I.

The compounds of formula I may be applied to the polyamide fibres, which may be, for example, in yarn, nonwoven, woven or knitted form, in conventional manner, for example for the so-called "thermosol" application method, (Gunn and Nightingale "Cotton and Man-Made Fibres Year Book" 1966–67, p. 410).

In such process the compounds are applied in amounts of from 0.01% to 0.7%, preferably 0.05% to 0.3% based on the weight of substrate. The substrate is padded with liquor at a temperature of from 0° to 60° C, preferably 10° to 50° C at the pick-up of from 20 to 120%, preferably 40 to 90%, the liquor containing such additives as surfactants and formic acid etc. as desired. The subsequent heat treatment applied for 5 to 120 secs, preferably 15 to 60 secs, the temperature being 140° to 190° C, preferably 160° to 185° C, for nylon 6 and 140° to 220° C, preferably 170° to 200° C for nylon 6,6.

The compounds give notably bright effects when applied by this method. Other methods include the so-called "acid flash" procedure and exhaust, acid or neutral bath, methods. In the "acid flash" procedure, the substrate, preferably of nylon 6 or nylon 6,6 is padded in similar manner to as described above for the "Thermosol" application method, whereafter the wet padded substrate is treated in a bath containing 0.05 to 1.0%, preferably 0.1 to 0.4% acid, usually an organic acid such as formic or acetic acid at 80° to 100° C, preferably 90° to 95° C, for a period of from 5 to 120 seconds, preferably from 5 to 60 seconds, and then dried.

The following Examples, in which all parts and percentages are by weight and all temperatures are in degrees centigrade, illustrate the invention.

EXAMPLE 1:

39.25 g of 1-(β-carboxyethylsulphonylphenyl)-3-p-chlorophenyl-Δ$^2$-pyrazoline was slurried in 250 ml trichloroethylene and the mixture heated to the boil. 0.2 ml of dimethylformamide was added to the mixture, followed by 15.0 g of thionyl chloride over a period of 15 minutes. The mixture was stirred under reflux for 2 hours, cooled to 10°–15°, filtered, and the filter cake washed with 25 ml cold trichloroethylene.

The filter cake of crude acid chloride thus obtained was dissolved in 150 ml of acetone and added over a period of 5 minutes to a well stirred solution of 16.1 g of N-methyl taurine sodium salt in 75 ml of water. The pH of the reaction mixture was maintained at 6.5 to 7.5 by the addition of sodium bicarbonate, and stirring was continued for 1 hour at ambient temperature. The mixture was heated to reflux, 25.0 g of sodium chloride added, and the resulting solution cooled to give the pyrazoline

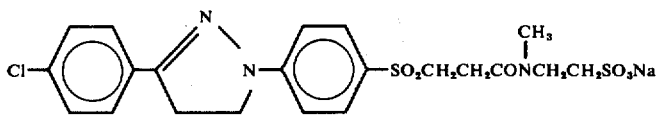

as a pale yellow solid.

EXAMPLE 2:

By repeating the procedure of Example 1 but using appropriate starting materials the compounds in the following table can be obtained.

| Ex. | Compound | Appearance |
|---|---|---|
| 2 | Cl-C6H4-CH=N-N-C6H4-SO2CH2CH2CONHCH2CH2SO3Na | pale yellow solid |
| 2a | F-C6H4-CH=N-N-C6H4-SO2CH2CH2CON(CH3)CH2CH2SO3Na | white solid |
| 2b | CH3O-C6H4-CH=N-N-C6H4-SO2CH2CH2CON(CH3)CH2CH2SO3Na | pale yellow solid |
| 2c | C6H5-CH=N-N-C6H4-SO2CH2CH2CON(CH3)CH2CH2SO3Na | white solid |
| 2d | Cl-C6H4-CH=N-N-C6H4-SO2CH2CH(CH3)CON(CH3)CH2CH2SO3Na | pale yellow solid |
| 2e | Cl-C6H4-CH=N-N-C6H4-SO2CH2CH2CH2CON(CH3)CH2CH2SO3Na | pale yellow solid |

EXAMPLE 3:

41.45 g of 1-(β-carboxyethylsulphonylphenyl)-3-p-chlorophenyl-Δ²-pyrazoline sodium salt was slurried in a mixture of 500 ml of dioxan and 15.0 g of propane sultone. The mixture was heated to the boil and stirred under reflux for 16 hours. The cooled mixture was filtered and washed with acetone to give the pyrazoline of formula

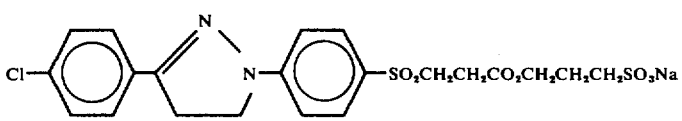

as an off-white solid.

By repeating the procedure of Example 3 but using appropriate starting materials the compounds in the following table can be obtained.

| Ex. | Compound | Appearance |
|---|---|---|
| 3a | NaO₃S—⌬—C(=N–N)—CH₂—N—⌬—SO₂CH₂CH₂CO₂CH₂CH₂CH₂SO₃Na | yellow solid |
| 3b | Cl—⌬—C(=N–N)—CH(C₆H₄SO₃Na)—N—⌬—SO₂CH₂CH₂CO₂CH₂CH₂CH₂SO₃Na | pale yellow solid |

EXAMPLE 4:

β-chloroethyl-(3,4-dichloro-6-methyl)-phenyl ketone (25.15g), 4-(β-carboxyethylsulphonyl)-phenyl hydrazine hydrochloride (26.05g) and sodium acetate (20.5g) were slurried together in glacial acetic acid (250 ml) and water (50 ml). The mixture was heated to the boil and stirred under reflux for four hours. The resultant mixture was cooled to 10° C and filtered to give 39.7g of 1-(β-carboxyethyl-sulphonyl)-phenyl-3-(3', 4'-dichloro-6'-methyl)-phenyl-Δ²-pyrazoline. The pyrazoline was dissolved in dioxan (200 ml) at 90°–100° C, and a solution of sodium hydroxide (4.0g) in water (12 ml) was added, and the mixture was cooled to 10° C and filtered. The wet cake was slurried in a mixture of dioxan (50 ml) and propane sultone (15.0g), heated to the boil, and stirred under reflux for 16 hours. The cooled mixture was filtered and washed with acetone to give the pyrazoline of formula

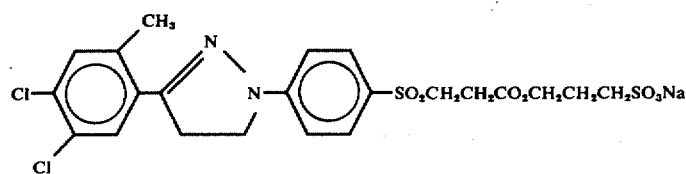

as an off white solid.

EXAMPLE 5:

40.7 g of the acid chloride of 1-(β-carboxyethylsul-phonylphenyl-3-(p-chlorophenyl)-Δ²-pyrazoline was dissolved in 300 ml of acetone and added over a period of 10 minutes to a well stirred solution of 20.0 g of sodium sulphanilate in 75 ml of water. The pH of the reaction mixture was maintained at 7 to 8 by the addition of sodium bicarbonate, and stirring was continued for one hour at ambient temperature. The mixture was then heated to reflux, 100 ml of water containing 10 g sodium chloride was added, and the resulting solution cooled to give the pyrazoline

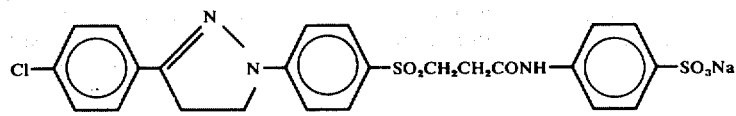

as a pale yellow solid.

EXAMPLE 6:

19.1 g of β-chloropropionyl chloride was added over a period of 15 minutes to a stirred solution of 24.15 g of N-methyl taurine sodium salt in 45 ml of water at 0°–5° C. The pH of the reaction mixture was maintained at 7–8 by the addition of sodium carbonate, and the temperature of the mixture was allowed to rise to 20° C over 1 hour. 6 g of sodium hydroxide in 15 ml of water was then added dropwise at 25°–30° C, and the mixture was stirred for 1 hour at 30° C. 39.1 g of 3-(3¹,4¹-dichloro-6¹-methyl)-phenyl-Δ²-pyrazoline-1-p-phenylsulphinic acid sodium salt, 100 ml water and 200 ml 2-ethoxyethanol were then added and the pH of the resultant mixture was adjusted to 5 with glacial acetic acid. The mixture was heated under reflux for 6 hours, while the pH was maintained at 5 by the occasional addition of glacial acetic acid. 20 g Sodium chloride was added to the hot mixture, which was then cooled to give the pyrazoline

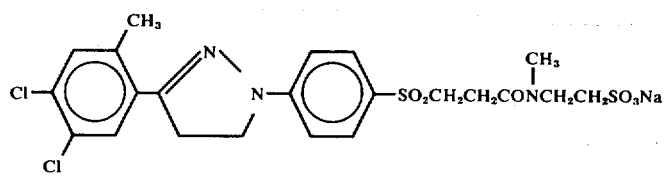

as a yellow solid.

The 3-(3',4'-dichloro-6'-methyl)-phenyl-Δ²-pyrazoline-1-(p-phenylsulphinic acid)-sodium salt was obtained as follows:-

3-(3',4'-dichloro-6'-methyl)-phenyl-Δ²-pyrazoline-1-phenylsulphonyl chloride (46.4g) was slurried in 2-ethoxyethanol (140 ml) and the mixture was added over 30 minutes to a solution of sodium sulphite (43.5g) in water (280 ml) at 70° C. The resultant mixture was stirred at 70° C for 1 hour, cooled, filtered and washed with 140 ml 5% brine to give a wet cake containing 39.1g of 3-(3',4'-dichloro-6'-methyl)-phenyl-Δ²-pyrazoline-(p-phenylsulphinic acid) sodium salt and approximately 30 g of water.

By repeating the procedure of Example 6 but using appropriate starting materials the compounds in the following table can be obtained.

EXAMPLE 7:

40.7 g of the acid chloride of 1-(β-carboxyethylsulphonylphenyl)-3-(p-chlorophenyl)-Δ²-pyrazoline and 15.0 g of isethionic acid sodium salt were slurried in 400 ml of chlorobenzene. The well stirred mixture was heated to reflux for 6 hours, and then cooled to give the pyrazoline

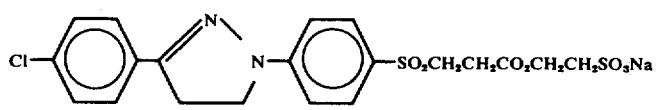

as an off-white solid.

EXAMPLE 8:

17.0 g of chloroacetyl chloride was added over a period of 15 minutes to a stirred solution of 24.15 g of N-methyl taurine sodium salt in 45 ml water at 0°–5° C. The pH of the reaction mixture was maintained at 7–8 by the addition of sodium carbonate, and the temperature of the mixture was allowed to rise to 20° C over 1

| Ex. | Compound | Appearance |
|---|---|---|
| 6a | ![structure] with CH₃, Cl, Cl substituents, —SO₂CH₂CH₂CONHCH₂CH₂SO₃Na | pale yellow solid |
| 6b | ![structure] with CH₃, Cl, Cl substituents, —SO₂CH₂CH₂CONH—C₆H₄—SO₃Na | pale yellow solid |
| 6c | ![structure] with CH₃, Cl, Cl substituents, —SO₂CH₂CH₂CON(CH₃)CH₂CH₂SO₃Na | off white solid |
| 6d | ![structure] with CH₃, (CH₃)₃C substituents, —SO₂CH₂CH₂CON(CH₃)CH₂CH₂SO₃Na | pale yellow solid |
| 6e | ![structure] with Cl substituent, —SO₂CH₂CH₂CON(C₂H₅)CH₂CH₂SO₃Na | pale yellow solid |
| 6f | ![structure] with Cl substituent, —SO₂CH₂CH₂CON(nC₄H₉)CH₂CH₂SO₃Na | pale yellow solid | hour. 34.25 g of 3-(p-chlorophenyl)-Δ²-pyrazoline-1-p-phenylsulphinic acid sodium salt, 100 ml water and 200 ml dimethylformamide were added and the resultant mixture was heated under reflux for 16 hours. 20 g of salt was added to the hot mixture, which was then cooled to give the pyrazoline

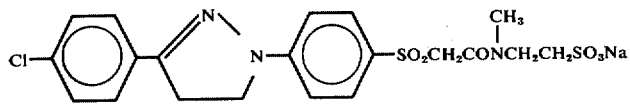

as a pale yellow solid.

EXAMPLE 9:

When the procedure described in Example 8 was repeated, using the sulphinic acid sodium salt employed in Example 6, the pyrazoline

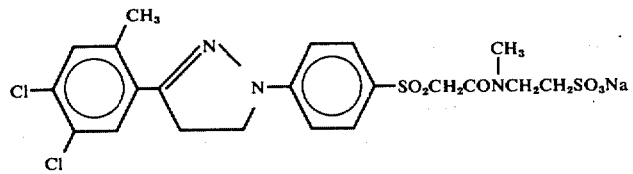

was obtained as a yellow solid.

EXAMPLE 10:

19.1 g of β-chloropropionyl chloride was added over a period of 15 minutes to a stirred solution of 29.3 g metanilic acid, sodium salt, in 75 ml of water at 0°–5° C. The pH of the reaction mixture was maintained at 7–8 by the addition of sodium carbonate, and the temperature of the mixture was allowed to rise to 20° C over 1 hour. 6 g of sodium hydroxide in 15 ml of water was then added dropwise at 25°–30° C, and the mixture was stirred for 1 hour at 30° C. 39.1 g of 3-(3¹,4¹-dichloro-6¹-methyl)-phenyl-Δ²-pyrazoline-1-p-phenylsulphinic acid sodium salt, 100 ml water and 200 ml 2-ethoxyethanol were then added and the pH of the resultant mixture was adjusted to 5 with glacial acetic acid. The mixture was heated under reflux for 6 hours, while the pH was maintained at 5 by the occasional addition of glacial acetic acid. 20 g sodium chloride was added to the hot mixture, which was then cooled to give the pyrazoline

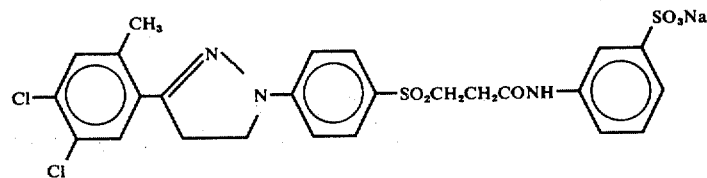

as a pale yellow solid.

By repeating the procedure of Example 10 but using appropriate starting materials the compounds in the following table can be obtained.

| Example | Compound | Appearance |
|---|---|---|
| 11 | ![structure] Cl-phenyl-pyrazoline-N-phenyl-SO₂(CH₂)₂CONH-phenyl-SO₃Na | pale yellow solid |
| 12 | ![structure] Cl-phenyl-pyrazoline-N-phenyl-SO₂CH₂CH₂CONH-phenyl-SO₃Na | off white solid |
| 13 | ![structure] Cl-phenyl-pyrazoline-N-phenyl-SO₂CH₂CH₂CONH-phenyl(CH₃)-SO₃Na | off white solid |

-continued

| Example | Compound | Appearance |
|---|---|---|
| 14 | Cl—C₆H₄—CH=N—N(CH₂—)—C₆H₄—SO₂CH₂CH₂CONH—C₆H₃(SO₃Na)(SO₃Na) | off white solid |
| 15 | Cl—C₆H₄—CH=N—N(CH(C₆H₅)—)—C₆H₄—SO₂CH₂CH₂CONH—C₆H₄—SO₃Na | pale yellow solid |
| 16 | Cl—C₆H₄—CH=N—N(CH(C₆H₅)—)—C₆H₄—SO₂CH₂CH₂CON(CH₃)CH₂CH₂SO₃Na | pale yellow solid |
| 17 | Cl—C₆H₄—CH=N—N(CH(CH₃)—)—C₆H₄—SO₂CH₂CH₂CONH—C₆H₄—SO₃Na | pale yellow solid |
| 18 | Cl—C₆H₄—CH=N—N(CH(4-Cl-C₆H₄)—)—C₆H₄—SO₂CH₂CH₂CONH—C₆H₄—SO₃Na | pale yellow solid |
| 19 | Cl—C₆H₄—CH=N—N(CH(4-CH₃-C₆H₄)—)—C₆H₄—SO₂CH₂CH₂CONH—C₆H₄—SO₃Na | pale yellow solid |
| 20 | Cl—C₆H₄—CH=N—N(CH(4-OCH₃-C₆H₄)—)—C₆H₄—SO₂CH₂CH₂CONH—C₆H₄—SO₃Na | pale yellow solid |
| 21 | Cl—C₆H₄—CH=N—N(CH₂—)—(3-Cl-C₆H₃)—SO₂CH₂CH₂CONH—C₆H₄—SO₃Na | pale yellow solid |

-continued
| Example | Compound | Appearance |
|---|---|---|
| 22 | 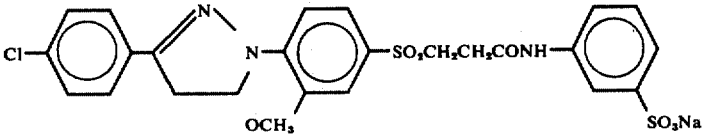 | pale yellow solid |
| 23 | 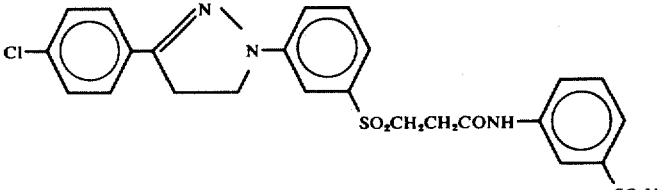 | pale yellow solid |
| 24 | 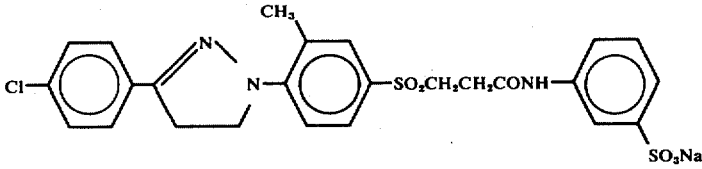 | pale yellow solid |
| 25 | 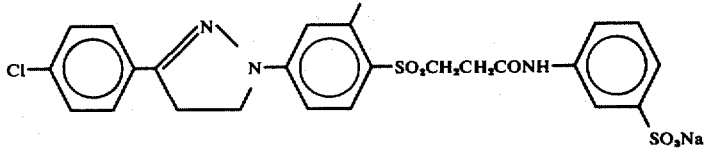 | pale yellow solid |
| 26 | 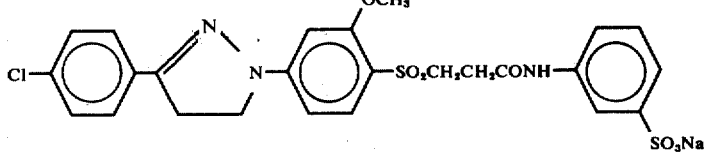 | pale yellow solid |
| 27 | 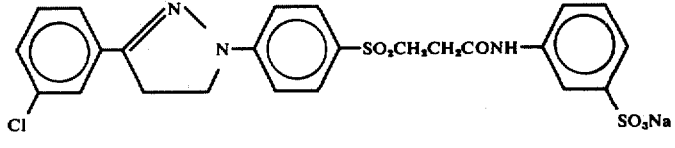 | pale yellow solid |
| 28 | 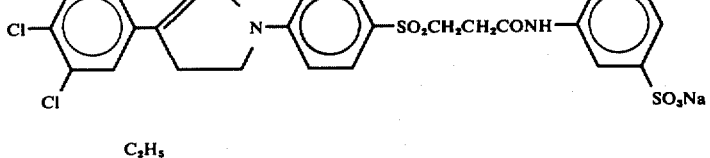 | yellow solid |
| 29 | 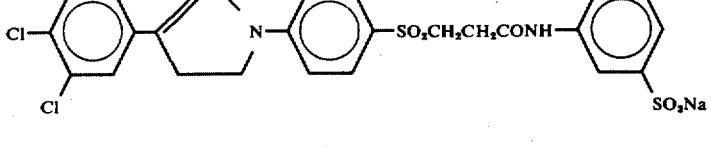 | pale yellow solid |
| 30 | 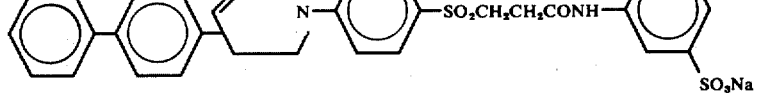 | yellow solid |

| Example | Compound | Appearance |
| --- | --- | --- |
| 31 | NC—⟨phenyl⟩—CH=N—N—⟨phenyl⟩—SO₂CH₂CH₂CONH—⟨phenyl-SO₃Na⟩ | yellow solid |
| 32 | CH₂(O,O)—⟨phenyl⟩—CH=N—N—⟨phenyl⟩—SO₂CH₂CH₂CONH—⟨phenyl-SO₃Na⟩ | pale yellow solid |

APPLICATION EXAMPLE A

A 5 gm piece of white nylon 6.6 was treated with 200 mls of a solution containing 25 milligrams of the pyrazoline produced in Example 1 and 150 mg of acetic acid. The piece was entered at 40°, the temperature of the bath increased to 90°–100° over 30 minutes and then maintained at 90°–100° for a further 30 minutes. The piece was removed from the bath, rinsed in cold demineralised water and dried in an oven at 80°. The treated piece showed a brilliant whiteness compared to the untreated piece.

APPLICATION EXAMPLE B

A strip of white nylon 6.6, 15 cc wide and weighing 8 gms, was padded at 100% expression through a solution containing 0.2% of the pyrazoline produced in Example 2, 2% of a non-ionic alkylene oxide adduct of an alkylated phenol, and 0.2% formic acid. The nylon piece was dried at 80° and then passed through an oven at 180° for 30 seconds. The treated piece showed a brilliant whiteness compared with the untreated piece.

APPLICATION EXAMPLE C

A strip of nylon 6.6, 15 cms wide and weighing 8 g, was padded at 100% expression through a solution containing 0.2% of the pyrazoline produced in Example 4. The nylon piece was boiled for 1 minute in 240 ml of water containing 0.2% acetic acid, and was then washed off in boiling water for 1 minute. The piece was then rinsed in cold demineralised water and dried in an oven at 80°. The treated piece showed a brilliant whiteness compared to the untreated piece.

APPLICATION EXAMPLE D:

A strip of white nylon 6.6, 15 cc wide and weighing 8 gms, was padded at 100% expression through a solution containing 0.2% of the pyrazoline produced in Example 5, 2% of a non-ionic alkylene oxide adduct of an alkylated phenol, and 0.2% formic acid. The nylon piece was dried at 80° and then passed through an oven at 180° for 30 seconds. The treated piece showed a brilliant whiteness compared with the untreated piece.

The procedure of Application Example D was repeated, but using 0.2% of the pyrazoline produced in Example 11. The treated piece of nylon showed a brilliant whiteness compared with the untreated piece.

APPLICATION EXAMPLE E:

A 5 gm piece of white nylon 6.6 was treated with 200 mls of a solution containing 25 milligrams of the pyrazoline produced in Example 6 and 150 mg of acetic acid. The piece was entered at 40°, the temperature of the bath increased to 90°–100° over 30 minutes and then maintained at 90°–100° for a further 30 minutes. The piece was removed from the bath, rinsed in cold demineralised water and dried in an oven at 80°. The treated piece showed a brilliant whiteness compared to the untreated piece.

APPLICATION EXAMPLE F:

A strip of nylon 6.6, 15 cms wide and weighing 8 g, was padded at 100% expression through a solution containing 0.2% of the pyrazoline produced in Example 7. The nylon piece was boiled for 1 minute in 240 ml of water containing 0.2% acetic acid, and was then washed off in boiling water for 1 minute. The piece was then rinsed in cold demineralised water and dried in an oven at 80°. The treated piece showed a brilliant whiteness compared to the untreated piece.

The procedure of Application Example F was repeated but using 0.2% of the pyrazoline produced in Example 10. The treated piece of nylon showed a brilliant whiteness compared with the untreated piece.

What is claimed is:

1. A compound of the formula,

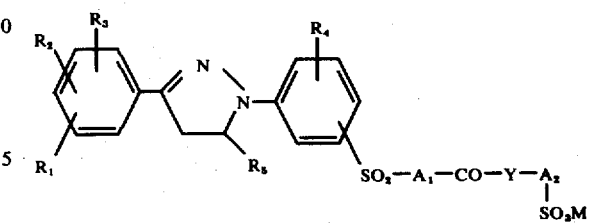

in which either $R_1$, $R_2$ and $R_3$, which may be the same or different, each signifies a hydrogen atom, a chloro or fluoro radical, an alkyl radical of 1 to 4 carbon atoms, an alkoxy radical of 1 to 4 carbon atoms, a cyano group, a group —SO₃M, an unsubstituted phenyl radical or a phenyl radical substituted by up to 2 substituents selected from chloro, fluoro, alkyl of 1 to 4 carbon atoms, alkoxy of 1 to 4 carbon atoms and the group —SO$_3$M, with the proviso that only one of R$_1$, R$_2$ and R$_3$ signifies an unsubstituted or substituted phenyl radical, or two of
R$_1$, R$_2$ and R$_3$ together form a methylenedioxy group, the other of R$_1$, R$_2$ and R$_3$ having one of the above significances, R$_4$ signifies a hydrogen atom, a chloro or fluoro radical, an alkyl radical of 1 to 4 carbon atoms or an alkoxy radical of 1 to 4 carbon atoms, R$_5$ signifies a hydrogen atom, an alkyl radical of 1 to 4 carbon atoms, an unsubstituted phenyl radical or a phenyl radical substituted by 1 or 2 substituents selected from chloro, fluoro, alkyl of 1 to 4 carbon atoms, alkoxy of 1 to 4 carbon atoms and the group —SO$_3$M, A$_1$ signifies a C$_1$ to C$_3$ alkylene chain, unsubstituted or substituted by up to two alkyl groups of 1 to 4 carbon atoms, A$_2$ signifies a C$_1$ to C$_3$ alkylene chain, unsubstituted or substituted by up to two alkyl groups of 1 to 4 carbon atoms; or a phenylene group, unsubstituted or substituted by up to 2 substituents selected from chloro, fluoro, alkyl of 1 to 4 carbon atoms, alkoxy of 1 to 4 carbon atoms and the group —SO$_3$M, Y signifies —O— or —NR$_6$—,

in which
R$_6$ signifies a hydrogen atom or an alkyl radical of 1 to 4 carbon atoms, and the Ms, which may be the same or different, each signifies a hydrogen atom, or a non-chromophoric cation.

2. A compound of claim 1, wherein any phenyl radical as R$_1$, R$_2$ or R$_3$, is unsubstituted.

3. A compound of claim 2, wherein R$_4$ signifies hydrogen.

4. A compound of claim 1, of the formula

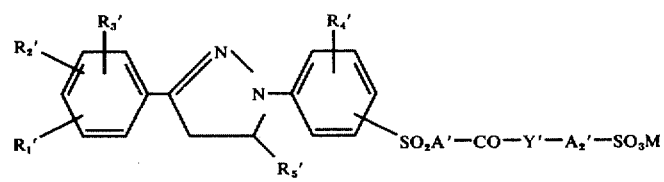

in which
R$_1'$, R$_2'$ and R$_3'$, independently, each signifies a hydrogen atom, a chloro or fluoro radical or an alkyl or alkoxy radical of 1 to 4 carbon atoms, R$_4'$ signifies a hydrogen atom, a chloro or fluoro radical or an alkyl or alkoxy radical of 1 to 4 carbon atoms, R$_5'$ signifies hydrogen, C$_{1-4}$ alkyl, or phenyl, A$_1'$ signifies an unsubstituted C$_1$–C$_3$ alkylene chain, A$_2'$ signifies an unsubstituted C$_1$–C$_3$ alkylene chain, a further unsubstituted phenylene radical or a phenylene radical further substituted by a —SO$_3$M or C$_{1-4}$ alkyl group, and Y' signifies —O— or $$-\underset{|}{\overset{R_6'}{N}}-$$

in which
R$_6'$ signifies a hydrogen atom or an alkyl radical of up to 2 carbon atoms.

5. A compound of claim 4, wherein R$_4'$ signifies a hydrogen atom.

6. A compound of claim 5, wherein, where R$_5'$ signifies a C$_{1-4}$ alkyl radical, such is a methyl radical.

7. A compound of claim 6, wherein the SO$_2$A$'$—CO—Y$'$—A$_2'$—SO$_3$M group is in the para position of the phenyl radical to which it is attached.

8. A compound of claim 4, of the formula

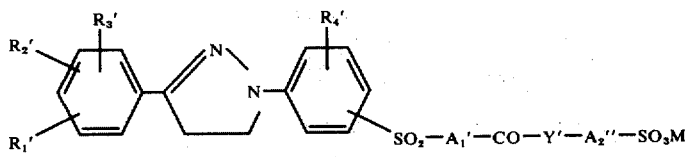

in which
A$_2''$ signifies an unsubstituted C$_{1-3}$ alkylene chain.

9. A compound of claim 8, wherein R$_4'$ signifies a hydrogen atom.

10. A compound of claim 8, wherein the —SO$_2$—A$'$—CO—Y$'$—A$_2''$—SO$_3$M group is in the para position of the phenyl radical to which it is attached.

11. A compound of claim 4, of the formula

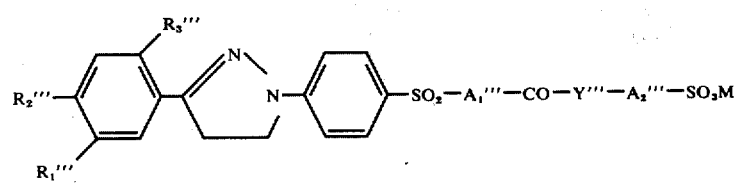

in which
R$_2'''$ signifies chloro and
either R$_1'''$ and R$_3'''$ both signify hydrogen,
or R$_1'''$ signifies chloro and
R$_3'''$ signifies methyl, $A_1'''$ signifies an unsubstituted alkylene radical of up to 2 carbon atoms, $Y'''$ signifies —O—, —NH— or

$A_2'''$ signifies a further unsubstituted phenylene radical, or an alkylene radical of two carbon atoms.

12. A compound of claim 11, wherein any phenylene radical as $A_2'''$ is a 1,4-phenylene radical.

13. A compound of claim 11, wherein any phenylene radical as $A_2'''$ is a 1,3-phenylene radical.

14. A compound of claim 4, of the formula

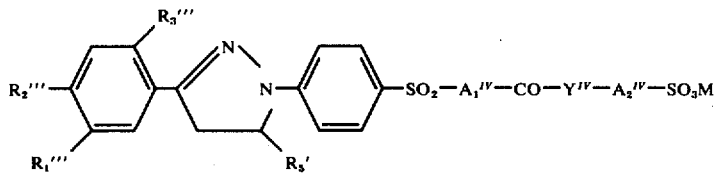

in which
$R_2'''$ signifies chloro, and
either $R_1'''$ and $R_3'''$ both signify hydrogen,
or $R_1'''$ signifies chloro and
$R_3'''$ signifies methyl,
$A_1^{IV}$ signifies an unsubstituted alkylene radical of up to 2 carbon atoms,
$A_2^{IV}$ signifies an ethylene group, a further unsubstituted phenylene radical or a phenylene radical substituted by a —SO₃M or $C_{1-4}$ alkyl group, and
$Y^{IV}$ signifies —O—, —NH— or

15. A compound of claim 14, wherein $A_1^{IV}$ signifies an alkylene radical of 2 carbon atoms.

16. A compound of claim 14, wherein, where $A_2^{IV}$ signifies a phenylene radical substituted by a $C_{1-4}$ alkyl radical, such is a phenylene radical substituted by a methyl radical.

17. A compound of claim 16, wherein $Y^{IV}$ signifies —NH— or —N(CH₃)-.

18. A compound of claim 8, of the formula

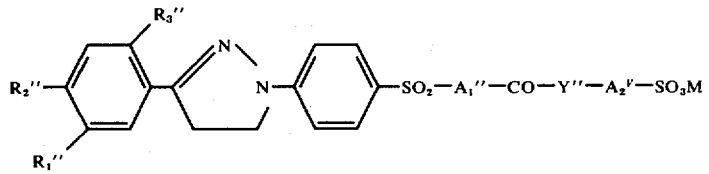

in which
$R_1''$, $R_2''$ and $R_3''$, which may be the same or different, each signifies a hydrogen atom, a chloro radical or an alkyl radical of up to 2 carbon atoms,
$Y''$ signifies —O—, —NH— or

$A_1''$ signifies an unsubstituted alkylene radical of up to 2 carbon atoms,
$A_2^V$ signifies an unsubstituted alkylene radical of 2 or 3 carbon atoms.

19. A compound of claim 17, of formula

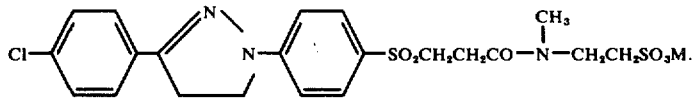

20. A compound of claim 17, of formula

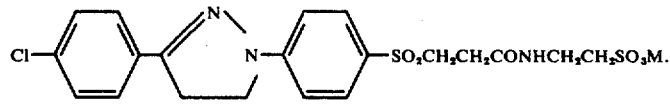

21. A compound of claim 17, of formula

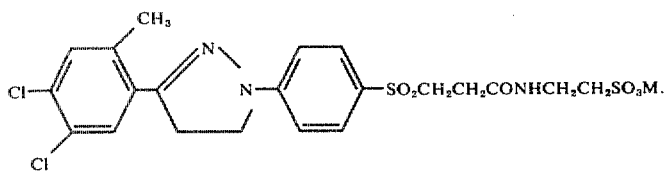

22. A compound of claim 17, of formula

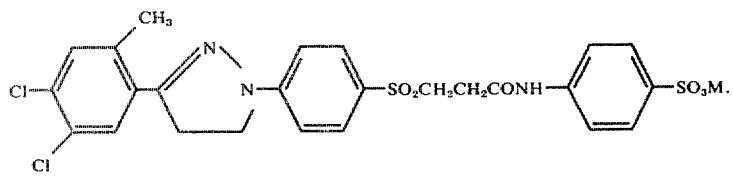

23. A compound of claim 17, of formula

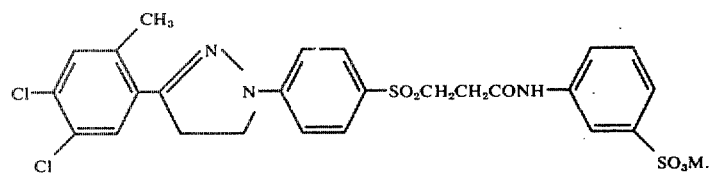

24. A compound of claim 17, of formula

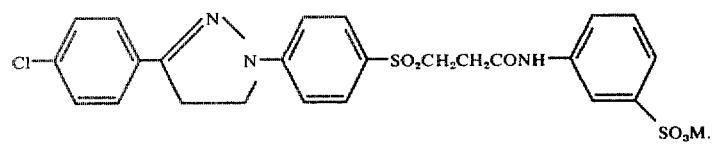

25. A compound of claim 17, of formula

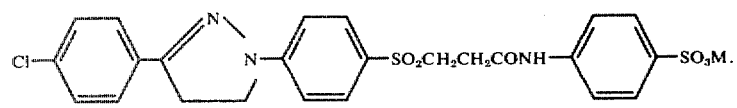

26. A compound of claim 1, in which M signifies a hydrogen atom, an alkali metal cation or a cation $R_7R_8R_9R_{10}N^+$, in which $R_7$, $R_8$, $R_9$ and $R_{10}$, independently, each signifies a hydrogen atom or an alkyl radical of 1 to 4 carbon atoms, unsubstituted or substituted by up to two substituents selected from alkyl of up to 2 carbon atoms and hydroxy.

27. A compound of claim 26, wherein, where M signifies a cation $R_7R_8R_9R_{10}N^+$, $R_{10}$ signifies hydrogen.

28. A compound of claim 27, wherein $R_7$, $R_8$ and $R_9$ signify hydrogen.

29. A compound of claim 26, wherein M signifies hydrogen or a sodium cation.

30. A compound of claim 29, wherein M signifies a sodium cation.

* * * * *